(12) United States Patent
Schmitt et al.

(10) Patent No.: US 9,464,298 B2
(45) Date of Patent: *Oct. 11, 2016

(54) EXPRESSION CASSETTE ENCODING A 5-ENOLPYRUVYLSHIKIMATE-3-PHOSPHATE SYNTHASE (EPSPS) AND HERBICIDE-TOLERANT PLANTS CONTAINING IT

(71) Applicant: Bayer S.A.S., Lyons (FR)

(72) Inventors: Frédéric Schmitt, Saint Didier de Formans (FR); Jean-Marc Ferullo, Berlin (DE); Alain Sailland, Saint Didier au Mont d'or (FR); Eric Paget, Caluire (FR)

(73) Assignee: BAYER S.A.S., Lyons (FR)

( * ) Notice: Subject to any disclaimer, the term of this patent is extended or adjusted under 35 U.S.C. 154(b) by 776 days.

This patent is subject to a terminal disclaimer.

(21) Appl. No.: 13/730,638

(22) Filed: Dec. 28, 2012

(65) Prior Publication Data

US 2013/0117893 A1 May 9, 2013

Related U.S. Application Data

(60) Continuation of application No. 12/569,068, filed on Sep. 29, 2009, now Pat. No. 8,536,408, which is a division of application No. 10/538,438, filed as application No. PCT/EP03/15008 on Dec. 10, 2003, now abandoned.

(30) Foreign Application Priority Data

Dec. 12, 2002 (FR) ...................................... 02 15695

(51) Int. Cl.
C12N 15/82 (2006.01)
(52) U.S. Cl.
CPC ................. *C12N 15/8275* (2013.01)
(58) Field of Classification Search
None
See application file for complete search history.

(56) References Cited

U.S. PATENT DOCUMENTS

| 6,566,587 B1 * | 5/2003 | Lebrun ............... C12N 15/8275 435/320.1 |
| 6,916,782 B1 * | 7/2005 | Lamberty ........ C07K 14/43563 435/440 |
| 7,129,343 B2 | 10/2006 | Li et al. |
| 8,536,408 B2 * | 9/2013 | Schmitt ............. C12N 15/8275 800/300 |
| 2004/0073966 A1 | 4/2004 | Zink et al. |

FOREIGN PATENT DOCUMENTS

| AU | 754856 B2 | 11/2002 |
| FR | 2 815 969 | 5/2002 |
| WO | WO-97/04103 | 2/1997 |
| WO | WO 97/04103 | * 2/1997 |
| WO | WO 97/48819 | * 12/1997 |
| WO | WO-97/48819 A1 | 12/1997 |
| WO | WO-99/53053 | 10/1999 |
| WO | WO-01/14573 | 3/2001 |

OTHER PUBLICATIONS

Calvert et al 1995, Journal of General Virology 76: 1271-1276.*
Whisstock, J.C. et al., "Prediction of Protein Function From Protein Sequence and Structure." *Quarterly Reviews of Biophysics* 36(3): 307-340 (Aug. 2003).
Padgette, S.R. et al., "Site-directed Mutagenesis of a Conserved Region of the 5-Enolpyruvylshikimate-3-phosphate Synthase Active Site." *The Journal of Biological Chemistry* 266(33): 22364-22369 (1991).
Verdaguer, B. et al., Isolation and Expression in Transgenic Tobacco and Rice Plants, of the Cassava Vein Mosaic Virus (CVMV) Promoter *Plant Molecular Biology* 31(6): 1129-1139 (1996).
Klee, H.J. et al., "Cloning of an Arabidopsis thaliana gene encoding 4-enolpyruvylshikimate-3-phosphate synthase: sequence analysis and manipulation to obtain glyphosate-tolerant plants." *Mol. Gen. Genet.* 210: 437-442 (Dec. 1987).
Pline, W.A. et al., "Effects of Temperature and Chemical Additives on the Response of Transgenic Herbicide-Resistant Soybeans to Glufosinate and Glyphosate Applications." *Pesticide Biochemistry and Physiology* 65: 119-131 (1999).
Shaner, D.L., "The impact of glyphosate-tolerant crops on the use of other herbicides and on resistance management." *Pest Management Science* 56: 300-326 (2000).

* cited by examiner

*Primary Examiner* — David H Kruse
(74) *Attorney, Agent, or Firm* — Arent Fox LLP

(57) ABSTRACT

The present invention relates to a novel expression cassette comprising a nucleic acid sequence encoding an EPSPS. In particular, the present invention relates to a novel expression cassette comprising, in the direction of transcription, functionally linked to one another, a promoter regulatory sequence which is functional in plant cells or plants, a nucleic acid sequence encoding an EPSPS and a terminator sequence which is functional in plant cells or plants, characterized in that the promoter regulatory sequence is a nucleic acid sequence chosen from the promoter regulatory sequences of the CsVMV (Cassava Vein Mosaic Virus) plant virus.

20 Claims, No Drawings

EXPRESSION CASSETTE ENCODING A 5-ENOLPYRUVYLSHIKIMATE-3-PHOSPHATE SYNTHASE (EPSPS) AND HERBICIDE-TOLERANT PLANTS CONTAINING IT

RELATED APPLICATIONS

This application is a continuation application of application Ser. No. 12/569,068, filed Sep. 29, 2009, which is a divisional application of application Ser. No. 10/538,438 filed Jan. 3, 2006, which is a national stage application (under 35 U.S.C. 371) of PCT/EP2003/015008 filed Dec. 10, 2003, which claims benefit to French application 0215695 filed Dec. 12, 2002. The entire contents of each of these applications are hereby incorporated by reference herein in their entirety.

The present invention relates to a novel expression cassette comprising a nucleic acid sequence encoding a 5-enolpyruvylshikimate-3-phosphate synthase (EPSPS) and to its use for obtaining plants resistant to herbicides which inhibit this enzyme, in particular herbicides of the phosphonic acid family, in particular of the N-phophonomethylglycine family.

STATE OF THE ART

One of the main problems in agriculture lies in controlling the development of undesirable self-propagating plants, or weeds, in areas where crops are grown. The development of weeds leads to a weakening of the crop plants and to a decrease in the yields from growing them. In order to combat these undesirable plants, herbicides are used, generally by spraying onto the crops.

Many types of herbicide exist, in particular selective herbicides which act only on a group of particular plants without affecting the crop plants. The disadvantage of selective herbicides is that their spectrum of activity is generally restricted, which requires the use of other selective herbicides with different spectra of activity in order to effectively control weeds. The solution to this disadvantage lies in the use of total herbicides capable of acting on all plants. Total herbicides are often herbicides for which the target is enzymes involved in the vital metabolic pathways of plants, which gives them the advantage of having a broad spectrum of activity on plants of distant phylogenetic origins. However, such herbicides also have the major disadvantage, when they are applied to crops in order to eliminate weeds, of also acting on the crop plants. This disadvantage may be overcome by using crop plants tolerant to said herbicides. Such plants are generally obtained by genetic engineering, by introducing into their genome a gene encoding an enzyme resistant to said herbicide so that they overexpress said enzyme in their tissues.

EPSPS is a plastid enzyme involved in the shikimate biosynthetic pathway, leading to the synthesis of aromatic amino acids. EPSPS is known to be the target enzyme for herbicides of the family of phosphonic acids of the phophonomethylglycine type. 5-enolpyruvylshikimate-3-phosphate synthase (EPSPS)-inhibiting herbicides are well known as being highly effective foliar herbicides. The most well known herbicide of this herbicide class is glyphosate [N-(phosphonomethyl)glycine]. Sulfonate or fosametine are also known. Glyphosate is characterized by a lack of selectivity for crop species and is, consequently, generally used under conditions in which there is no need for selectivity, for example as a total herbicide.

In order to overcome the problem of selectivity of glyphosate, plants tolerant to this herbicide have been developed by transformation of said plants with a gene encoding a glyphosate-tolerant EPSPS enzyme. Genes encoding glyphosate-tolerant EPSPS enzymes are in particular described in patent application EP 0837944. In particular, glyphosate-tolerant maize and soybean are sold respectively under the trade marks Roundup-Ready Corn™ and Roundup-Ready Soybean™. In this way, glyphosate can be applied to crops without affecting the crop plants which have been made tolerant thereto.

The success of this strategy is essentially based on the quality and the quantity of expression of the enzyme in the tissues of the plant intended to be made tolerant. These parameters of quality and quantity of expression are controlled by the regulatory elements introduced into the expression cassette with the nucleic acid sequence encoding said EPSPS enzyme. The regulatory elements essential to an expression cassette are the promoter regulatory sequence and the terminator regulatory sequence. The expression cassettes can also contain a signal peptide or a transit peptide, and also a transcription activator element or enhancer. However, the regulatory element which contributes most to the quality and the quantity of expression of a protein encoded by a nucleic acid sequence in an expression cassette is the promoter. Identification of the promoter suitable for expression of a given protein also depends largely on the nature of said protein, and in particular on the desired quantity and quality of expression of said protein. Associated with a given promotor is a quantity of expression of the product encoded by the nucleic acid sequence which it controls, and also a quality, in particular spatiotemporal quality, of this expression. In addition, some promoters are constitutive and others inducible.

An important characteristic for a promoter used in an expression cassette intended for the expression of an EPSPS enzyme in a plant is that it should allow a quantitative expression sufficient to confer tolerance to glyphosate on all the tissues of the plant which may be affected by this herbicide.

The technical problem of the present invention consists in obtaining an expression cassette in which the promoter is particularly suitable for the quantitative and qualitative expression of an EPSPS enzyme in transformed plants, said expression cassette then conferring effective tolerance on said plants, with respect to a herbicide which inhibits this enzyme, in particular a herbicide of the phophonomethylglycine family, in particular glyphosate.

Promoters which allow a high level of expression are generally promoters of highly expressed proteins. Among the most commonly used promoters satisfying these criteria, mention may be made, by way of example, of bacterial promoters, such as that of the octopine synthase gene or that of the nopaline synthase gene, viral promoters, such as that of the gene controlling transcription of cauliflower mosaic virus 35S or 19S RNAs (Odell et al., 1985, Nature, 313, 810-812), or promoters of the cassava vein mosaic virus (as described in patent application WO 97/48819). Among the promoters of plant origin, mention will be made of the promoter of the ribulose-biscarboxylase/oxygenase (RuBisCO) small subunit gene, the promoter of a histone gene described in application EP 0 507 698, or the promoter of a rice actin gene (U.S. Pat. No. 5,641,876).

Other promoters are expressed specifically in the cells of certain tissues. Such promoters are generally promoters which regulate the expression of proteins involved in the function of a particular tissue or organ. In plants, rootspecific promoters, such as, for example, that described in patent application WO 00/29594, flower-specific promoters, such as those described in patent applications WO 98/22593, WO 99/15679 or WO 99/43818, and fruit-specific promoters, in particular seed-specific promoters such as those described in patent applications WO 91/13993, WO 92/17580, WO 98/45460, WO 98/45461, or WO 99/16890, are known.

DESCRIPTION

The present invention relates to a novel expression cassette comprising, in the direction of transcription, functionally linked to one another, a promoter regulatory sequence which is functional in plant cells or plants, a nucleic acid sequence encoding 5-enolpyruvylshikimate-3-phosphate synthase (EPSPS) and a terminator sequence which is functional in plant cells or plants, characterized in that the promoter regulatory sequence is a nucleic acid sequence chosen from the promoter regulatory sequences of the CsVMV (Cassava Vein Mosaic Virus) plant virus.

The expression "functionally linked to one another" means that said elements of the chimeric gene are linked to one another in such a way that their function is coordinated and allows expression of the coding sequence. By way of example, a promoter is functionally linked to a coding sequence when it is capable of ensuring expression of said coding sequence. The construction of a chimeric gene according to the invention and the assembly of its various elements can be carried out using techniques well known to those skilled in the art, in particular those described in Sambrook et al. (1989, Molecular Cloning: A Laboratory Manual, Nolan C. ed., New York: Cold Spring Harbor Laboratory Press). The expression "functional in plant cells and plants" is intended to mean capable of functioning in plant cells and plants.

CsVMV promoter regulatory sequences are described in patent application WO 97/48819 (the content of which is incorporated herein by way of reference), in particular the promoter regulatory sequence comprising one of the nucleotide sequences represented by one of the sequence identifiers SEQ ID Nos. 1, 2, 3, 4, 5, 6, 7, 8, 9, 10, 11, 12, 13, 14, 15 or 16 of patent application WO 97/48819, more particularly the nucleic acid sequence represented by the sequence identifier SEQ ID NO 3 of patent application WO 97/48819.

According to a first preferred embodiment of the invention, the promoter regulatory sequence of the expression cassette comprises, in the direction of transcription, the nucleic acid sequences X, Y and Z as defined respectively by SEQ ID NOS 1, 2 and 3 of the present patent application.

According to the present invention, a preferred promoter regulatory sequence for the expression cassette is represented by SEQ ID NO 4 of the present patent application.

According to a second embodiment of the invention, the promoter regulatory sequence of the expression cassette comprises, in the direction of transcription, the nucleic acid sequences X, Y, Y and Z as defined above. The promoter regulatory sequence comprising the duplication of the nucleic acid sequence Y will be referred to as double CsVMV. Preferably, the nucleic acid sequence of the double CsVMV is represented by SEQ ID NO 5 of the present application.

The present invention also relates to the sequences capable of hybridizing selectively with the nucleic acid sequences above, the sequences homologous to the sequences above, and the functional fragments of said sequences.

According to the present invention, the term "nucleic acid sequence" is intended to mean a nucleotide or polynucleotide sequence which may be of the DNA or RNA type, preferably of the DNA type, in particular double-stranded.

According to the invention, the expression "sequence capable of hybridizing selectively" is intended to mean the sequences which hybridize with the sequences above at a level significantly greater than the background noise. The background noise may be related to the hybridization of other DNA sequences present, in particular other cDNAs present in a cDNA library. The level of the signal generated by the interaction between the sequence capable of hybridizing selectively and the sequences defined by the SEQ IDs above according to the invention is generally 10 times, preferably 100 times, more intense than that of the interaction of the other DNA sequences generating the background noise. The level of interaction can be measured, for example, by labeling the probe with radioactive elements, such as $^{32}$P. Selective hybridization is generally obtained using very stringent medium conditions (for example 0.03 M NaCl and 0.03 M sodium citrate at approximately 50° C.-60° C.). The hybridization can of course be carried out according to the usual methods of the state of the art (in particular Sambrook & al., 1989, Molecular Cloning: A Libratory Manual).

According to the invention, the term "homologue" is intended to mean a nucleic acid fragment exhibiting one or more sequence modifications relative to the nucleotide sequence encoding the fusion protein of the invention. These modifications may be obtained according to the usual mutation techniques, or else in choosing the synthetic oligonucleotides used in the preparation of said sequence by hybridization. With regard to the multiple combinations of nucleic acids which may lead to the expression of a same amino acid, the differences between the reference sequence according to the invention and the corresponding homologue may be considerable. Advantageously, the degree of homology will be at least 70% relative to the reference sequence, preferably at least 80%, more preferably at least 90%. These modifications are generally and preferably neutral, i.e. they do not affect the primary sequence of the fusion protein.

The methods for measuring and identifying homologies between nucleic acid sequences are well known to those skilled in the art. Use may, for example, be made of the PILEUP or BLAST programs (in particular Altschul & al., 1993, J. Mol. Evol. 36: 290-300; Altschul & al., 1990, J. Mol. Biol. 215: 403-10).

The methods for measuring and identifying homologies between polypeptides or proteins are also known to those skilled in the art. Use may, for example, be made of the UWGCG package and the BESTFITT program for calculating homologies (Deverexu & al., 1984, Nucleic Acid Res. 12, 387-395).

According to the invention, the term "fragments" is intended to mean fragments of the DNA sequences according to the invention, i.e. the sequences above for which parts have been deleted but which conserve the function of said sequences.

According to the invention, the term "EPSPS" is intended to mean any native or mutated 5-enolpyruvylshikimate-3-phosphate synthase enzyme, the enzymatic activity of which consists in synthesizing 5-O-(1-carboxyvinyl)-3-phosphoshikimate from phosphoenolpyruvate (PEP) and 3-phosphoshikimate (E.C. 2.5.1.19; Morell et al., 1967, J. Biol. Chem. 242, 82-90). In particular, said EPSPS enzyme may originate from any type of organism. An EPSPS enzyme according to the invention also has the property of being tolerant with respect to herbicides of the phophonomethylglycine family, in particular with respect to glyphosate.

Sequences encoding EPSPSs which are naturally tolerant, or are used as such, with respect to herbicides of the phophonomethylglycine family, in particular glyphosate, are known. By way of example, mention may be made of the sequence of the AroA gene of the bacterium *Salmonella typhimurium* (Comai et al., 1983, Science 221, 370-371), the sequence of the CP4 gene of the bacterium *Agrobacterium* sp. (WO 92/04449), or the sequences of the genes encoding Petunia EPSPS (Shah et al., 1986, Science 233, 478-481), Tomato EPSPS (Gasser et al., 1988, J. Biol. Chem. 263, 4280-4289), or Eleusine EPSPS (WO 01/66704).

Sequences encoding EPSPSs made tolerant to glyphosate by mutation are also known. By way of example, mention may be made of the sequences of the genes encoding mutated EPSPSs of bacterial origin (Stalker et al., 1985, J. Biol. Chem. 260 (8), 4724-4728), or of plant origin (EP 0293358; Ruff et al., 1991, Plant Physiol. 96(S), Abstract 592; WO 91/04323; WO 92/06201; EP 0837944). A sequence of a gene encoding a mutated plant EPSPS which is preferred according to the invention is that encoding the maize EPSPS described in patent application EP 0837944, comprising a first mutation replacing the threonine amino acid at position 102 with isoleucine, and a second mutation replacing the proline amino acid at position 106 with serine. Due to the strong sequence homology between EPSPSs, and more particularly between plant EPSPSs, a rice EPSPS carrying the same mutations have also been described in patent applications WO 00/66746 and WO 00/66747. In general, any EPSPS, and the genes encoding them, carrying the threonine/isoleucine and proline/serine mutations described above, whatever the relative position of these amino acids with respect to positions 102 and 106 of maize EPSPS, can be used in the present invention. To apply this principle, those skilled in the art will be readily able to find the two amino acids to be mutated in any EPSPS sequence by using standard techniques of sequence alignment.

According to a preferred embodiment of the invention, the nucleic acid sequence encoding an EPSPS included in the expression cassette is a sequence encoding an EPSPS which has been mutated at the amino acids corresponding to the threonine at position 102 and to the proline at position 106, said positions being relative with respect to the maize EPSPS sequence.

According to another preferred embodiment of the invention, the nucleic acid sequence encoding an EPSPS included in the expression cassette is a sequence encoding a mutated EPSPS comprising an isoleucine at position 102 and a serine at position 106, said positions being relative with respect to the maize EPSPS sequence.

According to another preferred embodiment of the invention, the nucleic acid sequence encoding an EPSPS included in the expression cassette is a sequence encoding maize mutated EPSPS comprising an isoleucine at position 102 and a serine at position 106.

Among the terminator sequences which can be used in the expression cassette according to the present invention, mention may be made, by way of example, of the nos terminator sequence of the gene encoding *Agrobacterium tumefaciens* nopaline synthase (Bevan et al., 1983, Nucleic Acids Res. 11 (2), 369-385), or the terminator sequence of a histone gene as described in application EP 0 633 317.

The expression cassette according to the invention may also comprise a subcellular addressing sequence encoding a signal peptide or transit peptide. Such a sequence, located upstream or downstream of the nucleic acid sequence encoding the EPSPS, makes it possible to direct said EPSPS specifically into a cellular compartment of the host organism. For example, the expression cassette may comprise a sequence encoding a signal peptide or a transit peptide for directing the EPSPS to a particular compartment of the cytoplasm, such as the mitochondria, the plants, the endoplasmic reticulum or the vacuoles.

The role of such sequences is in particular described in issue 38 of the revue Plant Molecular Biology (1998), devoted in large part to the transport of proteins into the various compartments of the plant cell (Sorting of proteins to vacuoles in plant cells pp 127-144; the nuclear pore complex pp 145-162; protein translocation into and across the chloroplastic enveloppe membranes pp 91-207; multiple pathways for the targeting of thylakoid proteins in chloroplasts pp 209-221; mitochondrial protein import in plants pp 311-338).

According to one embodiment, the transit peptide may be a signal for chloroplastic or mitochondrial addressing, which is then cleaved in the chloroplasts or the mitochondria.

The transit peptides may be either single or double transit peptides. The double transit peptides are optionally separated by an intermediate sequence, i.e. they comprise, in the direction of transcription, a sequence encoding a transit peptide of a plant gene encoding an enzyme which is located in plastids, a portion of sequence of the mature N-terminal portion of a plant gene encoding an enzyme which is located in plastids, and then a sequence encoding a second transit peptide of a plant gene encoding an enzyme which is located in plastids. Such double transit peptides are, for example, described in patent application EP 0 508 909.

According to the invention, the expression cassette may also comprise other regulatory sequences, which are located between the promoter and the coding sequence, such as transcription activators (enhancers), for instance the transcription activator of the tobacco mosaic virus (TMV) described in application WO 87/07644, of the tobacco etch virus (TEV) described by Carrington & Freed, or of the figwort mosaic virus (U.S. Pat. No. 5,994,521), for example. The expression cassette according to the invention may also contain introns, in particular introns which promote gene expression in monocotyledon plants, such as intron 1 of the rice actin gene described in patent application WO 99/34005, or the maize adh1 intron, or in dicotyledon plants, such as the *Arabidopsis* histone intron (EP 0850311).

The present invention also relates to a cloning an/or expression vector comprising an expression cassette according to the invention. The vector according to the invention is of use for transforming a host organism, in particular a plant, and expressing therein an EPSPS. This vector may be a plasmid, a cosmid, a bacteriophage or a virus. Preferably, the vector for transforming plant cells or plants according to the invention is a plasmid. In general, the main qualities of this vector should be an ability to maintain itself and to self-replicate in the cells of the host organism, in particular by virtue of the presence of an origin of replication, and to express therein an EPSPS. The choice of such a vector and also the techniques for inserting therein the expression cassette according to the invention are widely described in Sambrook et al. (1989, Molecular Cloning: A Laboratory Manual, Nolan C. ed., New York: Cold Spring Harbor Laboratory Press) and are part of the general knowledge of those skilled in the art. Advantageously, the vector used in the present invention also contains, in addition to the expression cassette according to the invention, another expression cassette containing a selection marker. This selection marker makes it possible to select the host organisms which have effectively been transformed, i.e. those which have incorporated the vector. According to a particular embodiment of the invention, the host organism to be transformed is a plant. Among the selection markers which can be used, mention may be made of markers containing genes resistant to antibiotics, such as, for example, that of the hygromycin phosphotransferase gene (Gritz et al., 1983, Gene 25:179-188), but also markers containing genes for tolerance to herbicides, such as the bar gene (White et al., NAR 18:1062, 1990) for tolerance to bialaphos, the EPSPS gene (EP 0837944) for tolerance to glyphosate or else the HPPD gene (WO 96/38567) for tolerance to isoxazoles. Mention may also be made of genes encoding readily identifiable enzymes such as the GUS enzyme, and genes encoding pigments or enzymes which regulate the production of pigments in the transformed cells. Such selection marker genes are in particular described in patent applications WO 91/02071, WO 95/06128, WO 96/38567, and WO 97/04103.

The present invention also relates to plant cells transformed with a vector as described above. The term "transformed plant cell" is intended to mean a plant cell which has incorporated into its genome the expression cassette according to the invention, and consequently produces an EPSPS. To obtain the transformed plant cells according to the invention, those skilled in the art may use one of the many known methods of transformation. One of these methods consists in bringing the plant cells to be transformed into contact with polyethylene glycol (PEG) and the vectors of the invention (Chang and Cohen, 1979, Mol. Gen. Genet. 168 (1), 111-115; Mercenier and Chassy, 1988, Biochimie 70 (4), 503-517). Electroporation is another method, which consists in subjecting the plant cells or tissues to be transformed and the vectors of the invention to an electric field (Andreason and Evans, 1988, Biotechniques 6 (7), 650-660; Shigekawa and Dower, 1989, Aust. J. Biotechnol. 3 (1), 56-62). Another method consists in directly injecting the vectors into the plant cells or the plant tissues by microinjection (Gordon and Ruddle, 1985, Gene 33 (2), 121-136). Advantageously, the "biolistic" method may be used. It consists in bombarding plant cells or plant tissues with particles onto which the vectors of the invention are absorbed (Bruce et al., 1989, Proc. Natl. Acad. Sci. USA 86 (24), 9692-9696; Klein et al., 1992, Biotechnology 10 (3), 286-291; U.S. Pat. No. 4,945,050). Preferably, the transformation of the plant cells will be carried out using bacteria of the genus *Agrobacterium*, preferably by infection of the cells or tissues of said plants with *A. tumefaciens* (Knopf, 1979, Subcell. Biochem. 6, 143-173; Shaw et al., 1983, Gene 23 (3):315-330) or *A. rhizogenes* (Bevan and Chilton, 1982, Annu. Rev. Genet. 16:357-384; Tepfer and Casse-Delbart, 1987, Microbiol. Sci. 4 (1), 24-28). Preferably, the transformation of plant cells with *Agrobacterium tumefaciens* is carried out according to the protocol described by Ishida et al. (1996, Nat. Biotechnol. 14 (6), 745-750). Those skilled in the art will choose the appropriate method according to the nature of the plant cells to be transformed.

A subject of the present invention is a method for producing plants tolerant to EPSPS-inhibiting herbicides, in particular to herbicides of the phophonomethylglycine family, in particular glyphosate. This method consists in regenerating transformed plants from the transformed plant cells described above. By this method, the transformed plants according to the invention contain an expression cassette according to the invention in their genome and express an EPSPS in their tissues.

The present invention therefore comprises transformed plants comprising an expression cassette according to the invention, parts of these plants, and the descendants of these plants. The expression "part of these plants" is intended to mean any organ of these plants, whether aerial or subterranean. The aerial organs are the stems, the leaves and the flowers. The subterranean organs are mainly the roots, but they may also be tubers. The term "descendants" is intended to mean mainly the seeds containing the embryos derived from the reproduction of these plants with one another. By extension, the term "descendants" applies to all the seeds formed at each new generation derived from crosses between a plant and the plant transformed by the method according to the invention.

A subject of the present invention is therefore transformed plants into the genome of which there is integrated at least one expression cassette according to the invention in a stable manner.

The plants thus transformed are tolerant to EPSPS-inhibiting herbicides, in particular herbicides of the phophonomethylglycine family, in particular to glyphosate.

The transformed plants according to the invention also include the transformed plants derived from growing and/or crossing the plants above, and also the seeds of such plants.

Of course, the transformed cells and plants according to the invention may comprise, in addition to an expression cassette according to the invention, at least one other expression cassette containing a polynucleotide encoding a protein of interest. Among the polynucleotides encoding a protein of interest, mention may be made of polynucleotides encoding another enzyme for resistance to a herbicide, for example the polynucleotide encoding the bar enzyme (White et al., NAR 18:1062, 1990) for tolerance to bialaphos, or the polynucleotide encoding the HPPD enzyme (WO 96/38567; WO 99/24585; WO 99/24586) for tolerance to isoxazoles. Mention may also be made of a polynucleotide encoding an insecticidal toxin, for example a polynucleotide encoding a toxin of the bacterium *Bacillus thuringiensis* (for example, see International Patent Application WO 98/40490). Other polynucleotides for resistance to diseases may also be contained in these plants, for example a polynucleotide encoding the oxalate oxydase enzyme as described in patent application EP 0 531 498 or U.S. Pat. No. 5,866,778, or a polynucleotide encoding an antibacterial and/or antifungal peptide such as those described in patent applications WO 97/30082, WO 99/24594, WO 99/02717, WO 99/53053, and WO 99/91089. Mention may also be made of polynucleotides encoding plant agronomic characteristics, in particular a polynucleotide encoding a delta-6 desaturase enzyme as described in U.S. Pat. Nos. 5,552,306 and 5,614,313, and patent applications WO 98/46763 and WO 98/46764, or a polynucleotide encoding a serine acetyltransferase (SAT) enzyme as described in patent applications WO 00/01833 and WO 00/36127.

The additional expression cassettes may be integrated by means of the vector according to the invention. In this case, the vector comprises the expression cassette according to the invention and at least one expression cassette encoding another protein of interest.

They may also be integrated by means of at least one other vector comprising said additional expression cassette, according to the usual techniques defined above.

The plants according to the invention may also be obtained by crossing parents, one carrying the expression cassette according to the invention, the other carrying another expression cassette encoding at least one other protein of interest.

The transformed plants according to the invention may be monocotyledons or dicotyledons. Preferably, these plants are plants of agronomic interest. Advantageously, the monocotyledon plants are wheat, maize or rice, advantageously, the dicotyledon plants are oilseed rape, soybean, tobacco or cotton.

The present invention also relates to a method for protecting crop plants with respect to EPSPS-inhibiting herbicides, in particular to herbicides of the phophonomethylglycine family, in particular to glyphosate, characterized in that said plants are transformed with a vector comprising an expression cassette according to the invention.

The present invention also relates to a method for treating the plants according to the invention, characterized in that said plants are treated with EPSPS-inhibiting herbicide, in particular a herbicide of the phophonomethylglycine family, in particular glyphosate.

The present invention also relates to a method for controlling weeds in crops, characterized in that transformed plants comprising an expression cassette according to the invention are grown, and in that said plants are treated with an EPSPS-inhibiting herbicide, in particular a herbicide of the phophonomethylglycinse family, in particular glyphosate.

The present invention also relates to a method for growing transformed plants comprising an expression cassette according to the invention, characterized in that it consists in planting seeds of said transformed plants in an area of a field suitable for growing said plants, in applying to said area of said field an agrochemical composition, without substantially affecting said transformed seeds or said transformed plants, then in harvesting the plants grown when they have reached the desired maturity and, optionally in separating the seeds from the harvested plants.

According to the invention, the term "agrochemical composition" is intended to mean any agrochemical composition comprising at least one active product having one of the following activities: herbicidal, fungicidal, bactericidal, virucidal or insecticidal.

According to a preferred embodiment of the method of growing according to the invention, the agrochemical composition comprises at least one active product having at least one herbicidal activity, more preferably an EPSPS-inhibiting herbicide, in particular a herbicide of the phophonomethylglycine family, in particular glyphosate.

The various aspects of the invention will be understood more clearly from the experimental examples below.

All the methods or operations described below in these examples are given by way of example and correspond to a choice made from the various available methods for achieving the same result. This choice has no bearing on the quality of the result and, consequently, any suitable method may be used by those skilled in the art to achieve the same result. In particular, and unless otherwise specified in the examples, all the recombinant DNA techniques used are carried out according to the standard protocols described in Sambrook et al. (1989, Molecular Cloning: A Laboratory Manual, Second edition, Nolan C. ed., Cold Spring Harbor Laboratory Press, NY), in Sambrook and Russel (2001, Molecular cloning: A laboratory manual, Third edition, Cold Spring Harbor Laboratory Press, NY), in Ausubel et al. (1994, Current Protocols in Molecular Biology, Current protocols, USA, Volumes 1 and 2), and in Brown (1998, Molecular Biology LabFax, Second edition, Academic Press, UK). Standard materials and methods for plant molecular biology are described in Croy R. D. D. (1993, Plant Molecular Biology LabFax, BIOS Scientific Publications Ltd (UK) and Blackwell Scientific Publications (UK)). Standard materials and methods for PCR (Polymerase Chain Reaction) are also described in Dieffenbach and Dveksler (1995, PCR Primer: A laboratory manual, Cold Spring Harbor Laboratory Press, NY) and in McPherson et al. (2000, PCR—Basics: From background to bench, First edition, Springer Verlag, Germany).

EXAMPLES

Example 1

Cloning of the CsVMV Promoter Sequence into the Multiple Cloning Vector pRD 254

The plasmid pILTAB 357 provided by The Scripps Research Institute (La Jolla, Calif., USA) contains the following elements in a pBIN 19 vector (Clontech):
  CsVMV promoter (sequence described by SEQ ID NO 4)
  multiple cloning site
  NOS terminator
  Three regions have been defined in the CsVMV promoter sequence, called CsVMV X, CsVMV Y and CsVMV Z.
  CsVMV X: from position 10 to position 227 (SEQ ID NO 1, length 218 bp)
  CsVMV Y: from position 228 to position 394 (SEQ ID NO 2, length 167 bp)
  CsVMV Z: from position 397 to position 522 (SEQ ID NO 3, length 126 bp)
  In the original sequence of the CsVMV promoter, the X and Y regions are adjacent and the Y and Z regions are separated by the 2 bp sequence AT.

The cloning vector pRD 254 corresponds to the commercial vector pBlueScript II SK (−) (Clontech) which has undergone mutagenesis so as to replace the unique Sca I site contained in the ApR gene with a Pvu II site.

The 532 bp contained between the Hind III and Xba I sites of pILTAB 357 were cloned into the cloning vector pRD 254, so as to obtain the plasmid pRD 257.

Example 2

Creation of a CsVMV-EPSPS Expression Cassette

An expression cassette introduced into a plasmid called pSF29 was developed.

The pSF29 cassette comprises the CsVMV promoter as described by the sequence identifier SEQ ID NO 4, the sequence encoding the optimized transit peptide (OTP) as defined in patent application EP 0508909, the sequence encoding maize EPSPS comprising the mutations threonine102isoleucine and proline106serine as described in patent application EP 0837944, and the nos terminator as described in Bevan et al. (1983, Nucleic Acids Res. 11 (2), 369-385).

Example 3

Integration of the Expression Cassette into an *Agrobacterium* T-DNA-Vector

A shuttle plasmid is used to be recombined in the superbinary plasmid pTVK 291 (Jun et al., 1987). Recombination between the unique COS sites present on the two plasmids produces a single circular molecule corresponding to fusion of the two plasmids.

Recombination between pSF29 and the superbinary plasmid pTVK 291 was obtained by three-parent crossing with DH5 alpha [pSF29], C2110 [pTVK 291], and the JC2073 strain ("helper" strain). The resulting plasmid is called pSFK29. The strain obtained, C2110 [pSFK29], was selected on LB medium containing the 3 antibiotics gentamycin, kanamycin and nalidixic acid. The nalidixic acid allows the selection of C2110 against DH5 alpha or JC2073; since C2110 contains a chromosomal resistance to nalidixic acid which cannot be transferred to the other strains during crossing. Combining gentamycin and kanamycin makes it possible to select the bacteria containing pSF29 and pTVK 291. In addition, pSF29 cannot replicate in C2110, unless it has been recombined with pTVK 291, since C2110 contains the origin of replication RK2 carried by pTVK 291, but not the origin of replication pBR 322 carried by pSF29.

The recombinant plasmid was then transferred into the *Agrobacterium* strain LBA 4404 via a second three-parent cross. The resultant strain, LBA 4404 [pSFK29], was selected on AB medium (selective for *Agrobacterium*) containing kanamycin and gentamycin.

Example 4

Transformation of Maize by *Agrobacterium tumefaciens* with a CsVMV-EPSPS Expression Cassette Transformation of the maize *Zea mays* by *Agrobacterium* is carried out according to the method described in Ishida, Y. et al., (1996, Nature Biotechnology, 14, 745-750). The disarmed *Agrobacterium tumefaciens* strain described in Example 3 is cocultured with immature maize embryos. A selection with 0.88 mM glyphosate is applied to the embryos. The transformation events obtained from the resistant calices are then back-crossed and their descendants are tested for glyphosate tolerance.

Example 5

Tests for Glyphosate Tolerance of the Transformation Events 20 seeds per event obtained were sown in a greenhouse in small pots in a rich compost, and a treatment post-emergence at the 3- to 4-leaf stage was carried out with a dose of glyphosate corresponding to 4 kg/ha (i.e. 4 kg of active material per 500 l) using a calibrated treatment tower. The events which survive the treatment are then counted. The results show that 90% of the transformation events containing the CsVMV-EPSPS expression cassette have plants capable of tolerating a dose corresponding to 4 kg/ha of glyphosate. A disparity in the number of tolerant plants for each event tested is due to the fact that these events are heterozygotes for the trait (the CsVMV-EPSPS expression cassette) and have one or more integration loci, and that some transformation events, by virtue of the position of insertion of the cassette, provide better expression of the EPSPS, and therefore better tolerance to glyphosate.

The invention claimed is:

1. A promoter regulatory sequence polynucleotide which is functional in plant cells or plants comprising, in the direction of transcription, the nucleic acid sequences X, Y, Y and Z, wherein (i) X, Y and Z are SEQ ID NO: 1, 2 and 3, respectively; or (ii) wherein X, Y and Z are SEQ ID NO: 1, 2 and 3, respectively, and at least one of the nucleic acid sequences X, Y or Z is a fragment of said nucleic acid sequence X, said nucleic acid sequence Y, or said nucleic acid sequence Z.

2. The promoter regulatory sequence polynucleotide of claim 1, wherein at least one of the nucleic acid sequences X, Y or Z is a fragment of said nucleic acid sequence X, said nucleic acid sequence Y, or said nucleic acid sequence Z.

3. The promoter regulatory sequence polynucleotide of claim 1, wherein one of the two Y nucleic acid sequences is a fragment of the Y nucleic acid sequence.

4. The promoter regulatory sequence polynucleotide of claim 1, wherein said promoter regulatory sequence polynucleotide is SEQ ID NO: 5.

5. An expression cassette comprising a polynucleotide, said polynucleotide comprising, in the direction of transcription, functionally linked to one another, the promoter regulatory sequence polynucleotide of claim 1, a nucleic acid sequence encoding an herbicide tolerance protein and a terminator regulatory sequence which is functional in plant cells or plants.

6. The expression cassette according to claim 5, wherein the nucleic acid sequence coding an herbicide tolerance protein is a nucleic acid sequence encoding an EPSPS protein.

7. The expression cassette according to claim 5, wherein the nucleic acid sequence polynucleotide encoding an EPSPS is a sequence polynucleotide encoding an EPSPS which has been mutated at the amino acids corresponding to the threonine at position 102 and to the proline at position 106, said positions being relative with respect to the maize EPSPS sequence.

8. The expression cassette as claimed in claim 7, wherein the nucleic acid sequence encoding an EPSPS is the sequence encoding a mutated EPSPS comprising an isoleucine at position 102 and a serine at position 106, said positions being relative with respect to the maize EPSPS sequence.

9. The expression cassette as claimed in claim 8, wherein the nucleic acid sequence encoding a mutated EPSPS is the sequence encoding a maize mutated EPSPS comprising an isoleucine at position 102 and a serine at position 106.

10. The expression cassette as claimed in claim 5, further comprising a double transit peptide comprising, in the direction of transcription, a sequence encoding a transit peptide of a plant gene encoding an enzyme which is located in plastids, a portion of sequence of the mature N-terminal portion of a plant gene encoding an enzyme which is located in plastids, and then a sequence encoding a second transit peptide of a plant gene encoding an enzyme which is located in plastids.

11. A cloning and/or expression vector for transforming plant cells or plants, wherein it comprises at least one expression cassette as claimed in claim 5.

12. A transformed plant cell, wherein it comprises an expression cassette as claimed in claim 5.

13. A transformed plant, wherein it comprises an expression cassette as claimed in claim 5.

14. A seed of a transformed plant as claimed in claim 13, wherein said seed comprises said expression cassette.

15. A method for treating plants as claimed in claim 13, wherein said plants are treated with an EPSPS-inhibiting herbicide.

16. The method as claimed in claim 15, wherein said EPSPS-inhibiting herbicide is glyphosate.

17. A method for controlling weeds in crops, comprising growing transformed plants as claimed in claim 13, and treating said plants with an EPSPS-inhibiting herbicide.

18. The method as claimed in claim 17, wherein said EPSPS-inhibiting herbicide is glyphosate.

19. A method for growing the transformed plaits plant as claimed in claim 13, comprising
    planting seeds of said transformed plants in an area of a field suitable for growing said plants,
    applying to said area of said field an agrochemical composition, without substantially affecting said transformed seeds or said transformed plants,
    harvesting the plants grown when they have reached the desired maturity and, optionally, separating the seeds from the harvested plants.

20. The promoter regulatory sequence polynucleotide of claim 1, wherein X, Y and Z are SEQ ID NO: 1, 2 and 3, respectively.

* * * * *

SEQUENCE LISTING

<160> NUMBER OF SEQ ID NOS: 5

<210> SEQ ID NO 1
<211> LENGTH: 219
<212> TYPE: DNA
<213> ORGANISM: Cassava vein mosaic virus

<400> SEQUENCE: 1
agaaggtaat tatccaagat gtagcatcaa gaatccaatg tttacgggaa aaactatgga 60
agtattatgt gagctcagca agaagcagat caatatgcgg cacatatgca acctatgttc 120
aaaaatgaag aatgtacaga tacaagatcc tatactgcca gaatacgaag aagaatacgt 180
agaaattgaa aaagaagaac caggcgaaga aaagaatct 219

<210> SEQ ID NO 2
<211> LENGTH: 168
<212> TYPE: DNA
<213> ORGANISM: Cassava vein mosaic virus

<400> SEQUENCE: 2
tgaagacgta agcactgacg acaacaatga aaagaagaag ataaggtcgg tgattgtgaa 60
agagacatag aggacacatg taaggtggaa aatgtaaggg cggaaagtaa ccttatcaca 120
aaggaatctt atcccccact acttatcctt ttatattttt ccgtgtca 168

<210> SEQ ID NO 3
<211> LENGTH: 127
<212> TYPE: DNA
<213> ORGANISM: Cassava vein mosaic virus

<400> SEQUENCE: 3
tttttgccct tgagttttcc tatataagga accaagttcg gcatttgtga aaacaagaaa 60
aaatttggtg taagctattt tctttgaagt actgaggata caacttcaga gaaatttgta 120

-continued agtttgt 127

<210> SEQ ID NO 4
<211> LENGTH: 538
<212> TYPE: DNA
<213> ORGANISM: Cassava vein mosaic virus

<400> SEQUENCE: 4
aagcttccag aaggtaatta tccaagatgt agcatcaaga atccaatgtt tacgggaaaa      60
actatggaag tattatgtga gctcagcaag aagcagatca atatgcggca catatgcaac     120
ctatgttcaa aaatgaagaa tgtacagata caagatccta tactgccaga atacgaagaa     180
gaatacgtag aaattgaaaa agaagaacca ggcgaagaaa agaatcttga agacgtaagc     240
actgacgaca acaatgaaaa gaagaagata aggtcggtga ttgtgaaaga gacatagagg     300
acacatgtaa ggtggaaaat gtaagggcgg aaagtaacct tatcacaaag gaatcttatc     360
ccccactact tatcctttta tattttccg tgtcattttt gcccttgagt tttcctatat      420
aaggaaccaa gttcggcatt tgtgaaaaca agaaaaaatt tggtgtaagc tattttcttt     480
gaagtactga ggatacaact tcagagaaat ttgtaagttt gtagatctcg attctaga      538

<210> SEQ ID NO 5
<211> LENGTH: 710
<212> TYPE: DNA
<213> ORGANISM: Artificial Sequence
<220> FEATURE:
<223> OTHER INFORMATION: Synthetic CsVMV sequence

<400> SEQUENCE: 5
aagcttccag aaggtaatta tccaagatgt agcatcaaga atccaatgtt tacgggaaaa      60
actatggaag tattatgtga gctcagcaag aagcagatca atatgcggca catatgcaac     120
ctatgttcaa aaatgaagaa tgtacagata caagatccta tactgccaga atacgaagaa     180
gaatacgtag aaattgaaaa agaagaacca ggcgaagaaa agaatcttga agacgtaagc     240
actgacgaca acaatgaaaa gaagaagata aggtcggtga ttgtgaaaga gacatagagg     300
acacatgtaa ggtggaaaat gtaagggcgg aaagtaacct tatcacaaag gaatcttatc     360
ccccactact tatcctttta tattttccg tgtcactagt gaagacgtaa gcactgacga      420
caacaatgaa aagaagaaga taaggtcggt gattgtgaaa gagacataga ggacacatgt     480
aaggtggaaa atgtaagggc ggaaagtaac cttatcacaa aggaatctta tcccccacta     540
cttatccttt tatattttc cgtgtcattt ttgcccttga gttttcctat ataaggaacc     600
aagttcggca tttgtgaaaa caagaaaaaa tttggtgtaa gctattttct ttgaagtact     660
gaggatacaa cttcagagaa atttgtaagt ttgtagatct cgattctaga                710